(12) United States Patent
Endres

(10) Patent No.: US 12,714,781 B2
(45) Date of Patent: Aug. 25, 2026

(54) AMBULATORY INFUSION PUMP WITH CONFIGURABLE BATTERY COMPARTMENT AND COVER

(71) Applicant: B. BRAUN MEDICAL INC., Bethlehem, PA (US)

(72) Inventor: Elisha James Endres, Bethlehem, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 614 days.

(21) Appl. No.: 18/137,710

(22) Filed: Apr. 21, 2023

(65) Prior Publication Data

US 2024/0350723 A1 Oct. 24, 2024

(51) Int. Cl.
*A61M 5/142* (2006.01)

(52) U.S. Cl.
CPC ..... *A61M 5/142* (2013.01); *A61M 2205/3334* (2013.01); *A61M 2205/8206* (2013.01); *A61M 2205/8237* (2013.01)

(58) Field of Classification Search
CPC .............. A61M 5/142; A61M 5/14244; A61M 2205/3334; A61M 2205/8206; A61M 2205/8237; H01M 50/213; H01M 50/247; H01M 50/264; H01M 50/271; H01M 50/291; H01M 2220/30
See application file for complete search history.

(56) References Cited

U.S. PATENT DOCUMENTS

| | | | | |
|---|---|---|---|---|
| 6,206,836 | B1 | 3/2001 | Kern et al. | |
| 6,352,322 | B1 * | 3/2002 | Nakao | G06F 1/1626 348/794 |
| 8,562,565 | B2 | 10/2013 | Fonacier et al. | |
| 8,603,032 | B2 | 12/2013 | Cheney et al. | |
| 8,603,033 | B2 | 12/2013 | Bazargan et al. | |
| 8,841,012 | B2 | 9/2014 | Fonacier et al. | |
| 9,011,355 | B2 | 4/2015 | Ehrenreich et al. | |
| 9,231,617 | B2 | 1/2016 | Cheney et al. | |
| 10,092,690 | B2 | 10/2018 | Gillespie et al. | |
| 10,610,609 | B2 | 4/2020 | Swaney et al. | |

(Continued)

FOREIGN PATENT DOCUMENTS

| | | |
|---|---|---|
| WO | 2014149954 A1 | 9/2014 |
| WO | 2020167843 A1 | 8/2020 |

OTHER PUBLICATIONS

International Search Report and Written Opinion for International Application No. PCT/US2024/022713, dated Jul. 24, 2024 (Jul. 24, 2024)—14 pages.

*Primary Examiner* — William H Rodriguez
(74) *Attorney, Agent, or Firm* — CM Law; Stephen J. Weed

(57) ABSTRACT

An ambulatory pump and a battery compartment for use in an ambulatory pump. The ambulatory pump includes a pump, a controller coupled to the pump for controlling the pump to deliver fluid to a patient, and a battery compartment electrically coupled to the pump and the controller. The battery compartment defines a cavity for alternately receiving a battery pack and a plurality of household batteries. The battery compartment is covered by an access cover that includes one or more rotatable retaining members that allow for the cavity to accept and hold the battery pack or household batteries.

20 Claims, 14 Drawing Sheets

(56) References Cited

U.S. PATENT DOCUMENTS

| | | | | |
|---|---|---|---|---|
| 11,090,426 | B2 | 8/2021 | Smith et al. | |
| 2005/0026035 | A1* | 2/2005 | Ishikawa ............. | H01M 50/264<br>206/703 |
| 2006/0040172 | A1* | 2/2006 | Hsu ..................... | H01M 50/227<br>429/96 |
| 2014/0228721 | A1 | 8/2014 | Ehrenreich et al. | |
| 2015/0305974 | A1 | 10/2015 | Ehrenreich et al. | |
| 2021/0023247 | A1 | 1/2021 | Swaney et al. | |
| 2021/0146033 | A1 | 5/2021 | Smith et al. | |
| 2022/0125968 | A1 | 4/2022 | Swaney et al. | |
| 2023/0001094 | A1 | 1/2023 | Schwarz et al. | |

* cited by examiner

AMBULATORY INFUSION PUMP WITH CONFIGURABLE BATTERY COMPARTMENT AND COVER

BACKGROUND

Infusion pumps deliver controlled doses of fluids such as medications, analgesics, and nutrition to patients. Infusion pumps are particularly well suited to delivering controlled doses over long periods of time, e.g., several hours or days. In addition to delivering fluids over long periods of time, an infusion pump can be used to deliver fluids on a timed schedule. The fluids being provided by the infusion pumps are often vital to the patient's stabilization and/or recovery.

While many infusion pumps are designed for bedside use, there are ambulatory versions available. Ambulatory infusion pumps allow a patient to move around while the infusion pump is in use. This can be beneficial for patients who would otherwise be confined to a bed, and it can help patients get some light exercise by walking or stretching. This also allows medications and nutrition to be delivered while patients are being transferred.

Ambulatory infusion pumps require a portable power source in order to continuously deliver vital medications and nutrition while mobile. Due to the vital nature of the medications and nutrition and the need for their continuous delivery, there is a need for improved power delivery systems.

SUMMARY

Examples described herein are directed to an ambulatory pump and a battery compartment for use in an ambulatory pump. The ambulatory pump includes a pump, a controller coupled to the pump for controlling the pump to deliver fluid to a patient, a battery compartment electrically coupled to the pump and to the controller, and an access cover. The battery compartment defines a cavity for alternately receiving a battery pack and household batteries. The access cover includes at least one retaining member that is rotatably coupled to the underside of the access cover. The retaining member has a profile that is configured to hold the plurality of household batteries or move out of the way for the battery pack when the access cover is closed.

DRAWINGS

The drawing figures depict multiple views of one or more implementations, by way of example only, not by way of limitations. In the figures, like reference numerals refer to the same or similar elements. The same numeral is used to represent the same or similar element across the multiple views. If multiple elements of the same or similar type are present, a small letter may be used to distinguish between the multiple elements. When the multiple elements are referred to collectively or a non-specific one of the multiple elements is being referenced, the small letter designation may be dropped.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Figure 1:
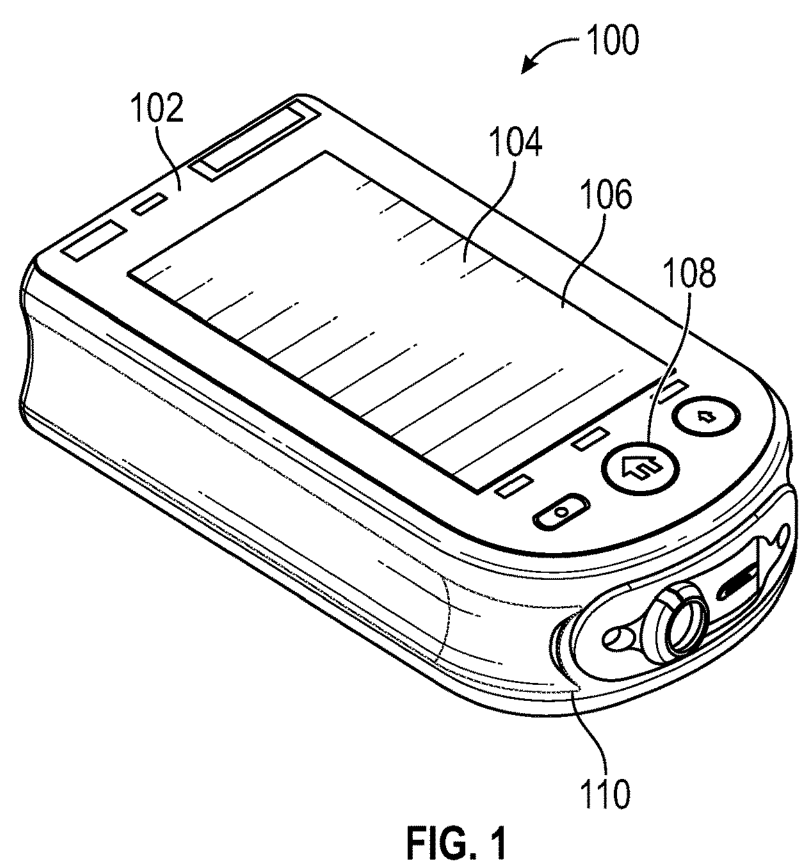
FIG. 1 is a perspective front view of an ambulatory infusion pump.

FIG. 1 depicts an example ambulatory pump 100. The pump 100 includes a peristaltic pump mechanism (not shown in FIG. 1) for pumping fluid from a fluid container (e.g., a bag or a bottle) into a patient. The pump 100 has a front face 102 that includes a user interface 104 for interacting with the pump 100. The illustrated user interface 104 includes a display 106 (which may be a touchscreen) and buttons 108. A user controls operation of the pump via the user interface 104. The pump 100 additionally includes a housing 110 for containing and supporting the components of the pump 100.

Figure 2:
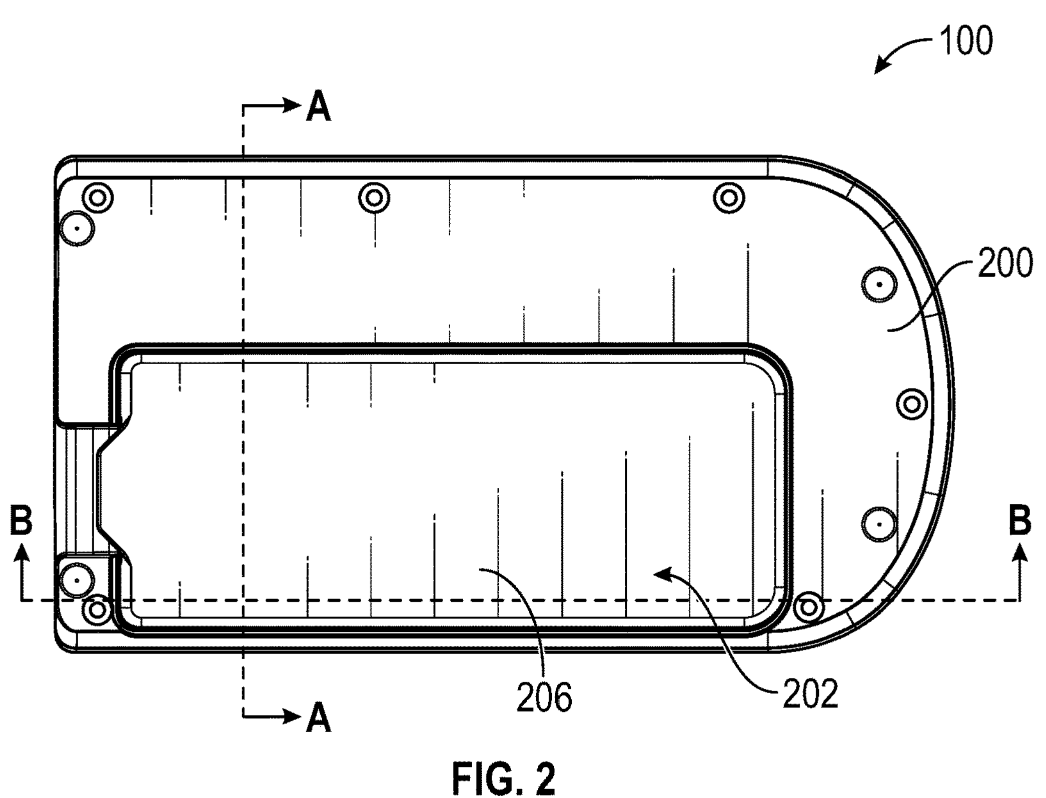
FIG. 2 is a back plan view of the ambulatory infusion pump of FIG. 1.

FIG. 2 depicts a back face 200 of the pump 100. An access cover 202 is positioned on the back face 200 of the pump and has an outer surface 206. Removing the access cover 202 provides access to a battery compartment for receiving alternate power sources (e.g., household batteries and a battery pack), which is described in further detail below.

Figure 3A:
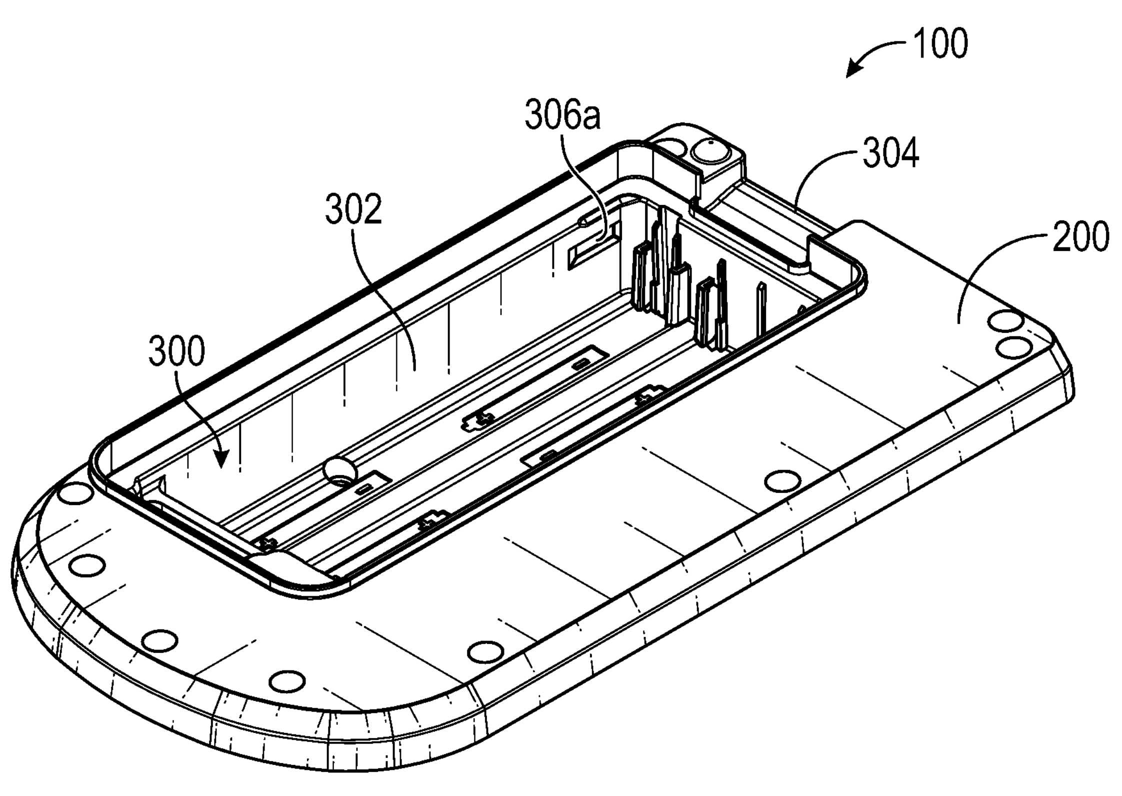
FIG. 3A is a back perspective view of the example ambulatory infusion pump of FIG. 1 with back cover removed in a household battery configuration with household batteries not installed.
Figure 3B:
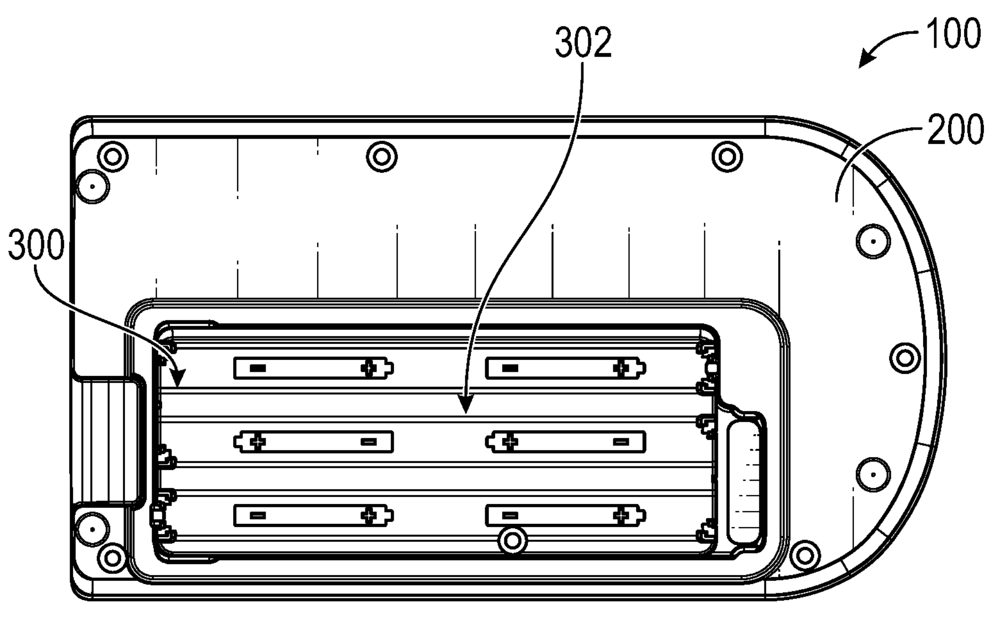
FIG. 3B is a back plan view of the example ambulatory infusion pump of FIG. 3.

FIG. 3A depicts the back of the pump 100 with the access cover 202 removed to reveal a battery compartment 300. The battery compartment 300 includes a cavity 302 sized to receive alternate power sources. The cavity 302 is sized to receive household batteries (six AA batteries in the illustrated example) or a battery pack configured to fit in the area required for the household batteries. Although the examples are illustrated using AA cylindrical household batteries, other types of household batteries may be used such as AAA, AA, C, D, and 9-volt type batteries. Suitable modifications to the cavity 302 and electrical connectors (not shown) to accommodate alternative household batteries will be understood by one of skill the art from the description herein. FIG. 3B is a back plan view of the example of FIG. 3A further illustrating the battery configuration in the example which is depicted as a 3×2 arrangement of AA household batteries.

Figure 4A:
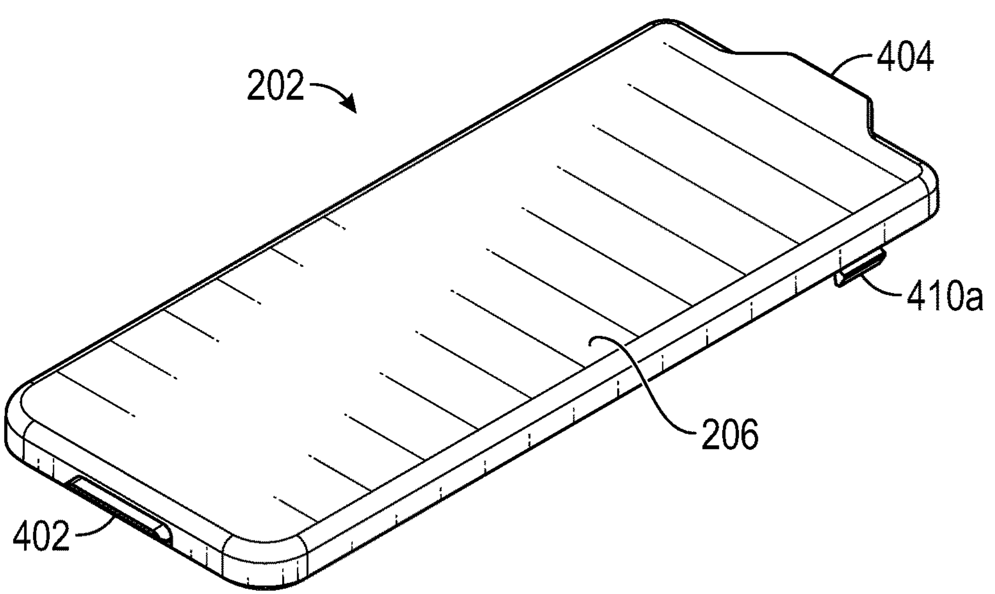
FIG. 4A is a perspective view of the top or outside of the access cover of the battery compartment.

FIG. 4A is a perspective view of the top or outer side or surface 206 of the access cover 202 of the battery compartment 300. The access cover 202 includes a first end 402 and a second end 404. The first end is configured to be toed-in or otherwise releasably attached to the battery compartment 300. In an example, the second end 404 is configured for engagement with latching mechanism 304 to close the battery compartment. The latching mechanism is further shown in FIGS. 4B and 4C.

Figure 4B:
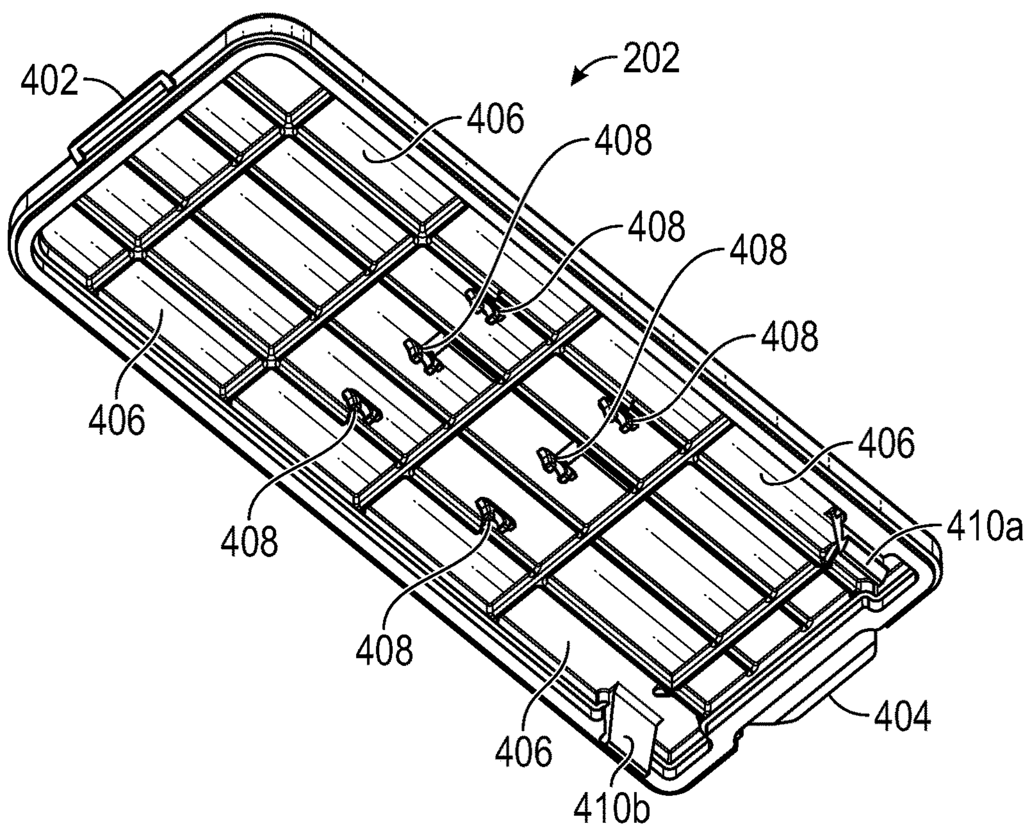
FIG. 4B is a perspective view showing the bottom or underside of the access cover of the battery compartment.
Figures 4C, 4D:
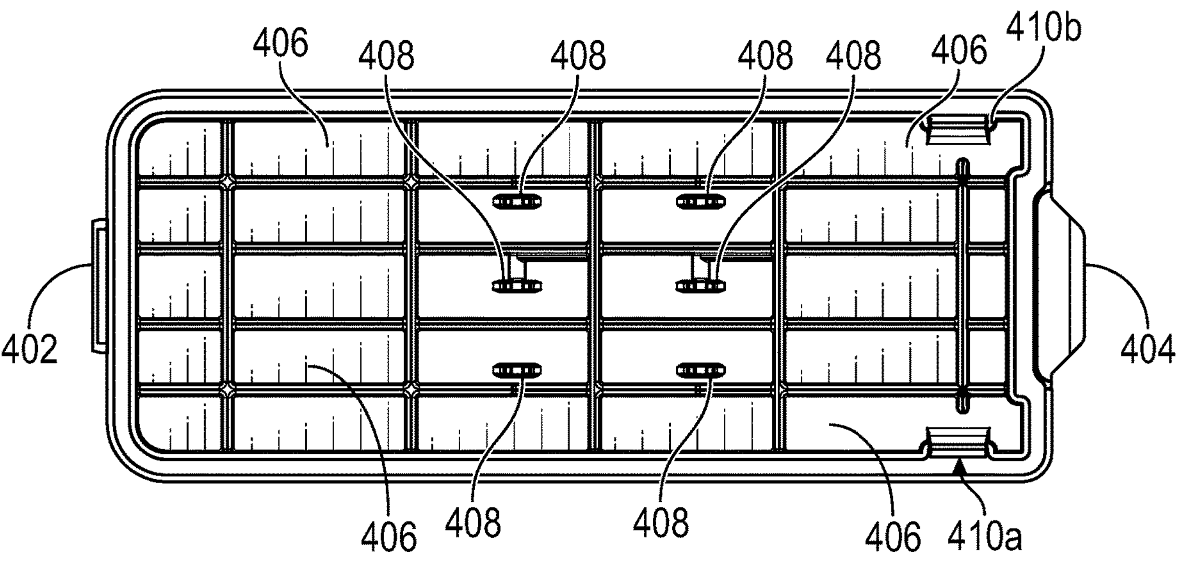
FIG. 4C is a bottom plan view of the access cover of the battery compartment.
FIG. 4D is an end elevation view of the access cover of the battery compartment.

FIGS. 4B and 4C depict in perspective and plan views the underside 406 of the access cover 202. In the illustrated example, the underside 406 of the access cover 202 includes a pair of spaced apart snap arms 410*a,b* that are configured to be received by a corresponding pair of recesses 306*a* (see FIG. 3A; 306*b* is not shown) each configured for engagement of a snap arm 410*a,b* to form latching mechanism 304. Also shown are the attachment points 408 for retaining members (discussed below). In the example depicted, the attachment points 408 are arranged in two rows of three attachment points.

Figure 4E:
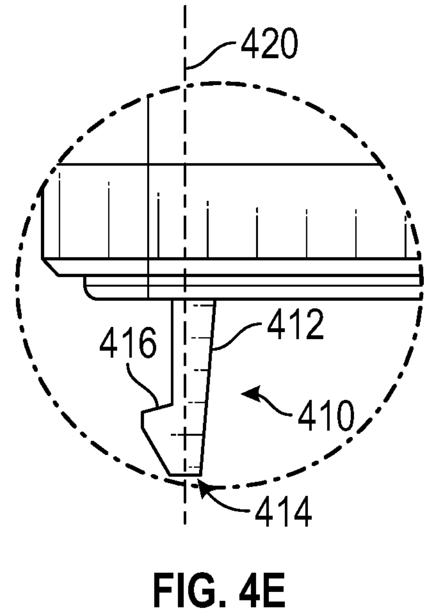
FIG. 4E is a detailed view of the snap arm shown in FIG. 4D.

FIG. 4D is an end elevation view of access cover 202 showing second 404 and the side profile of snap arms 410*a,b*. Snap arm 410*a* is shown in further detail in FIG. 4E. The description is similar for snap arm 410*b*. Body 412 of snap arm 410*a* extends perpendicularly from the underside surface along a longitudinal axis 420 and terminates in a head 414 in a "half-arrow" configuration. Cutback 416 of head 414 forms a detent that is sized to received by recess 306*a* to hold the access cover 202 when it is in the closed position covering the battery compartment. In one example, the cutback 416 is angled at greater than 90 degrees with respect to the longitudinal axis of the body that reduces the force necessary for a user to disengage the snap arm 410*a* from recess 306*a* (or 306*b* regarding snap arm 410*b*) to lift the access cover away from the compartment into the open position.

Figure 5A:
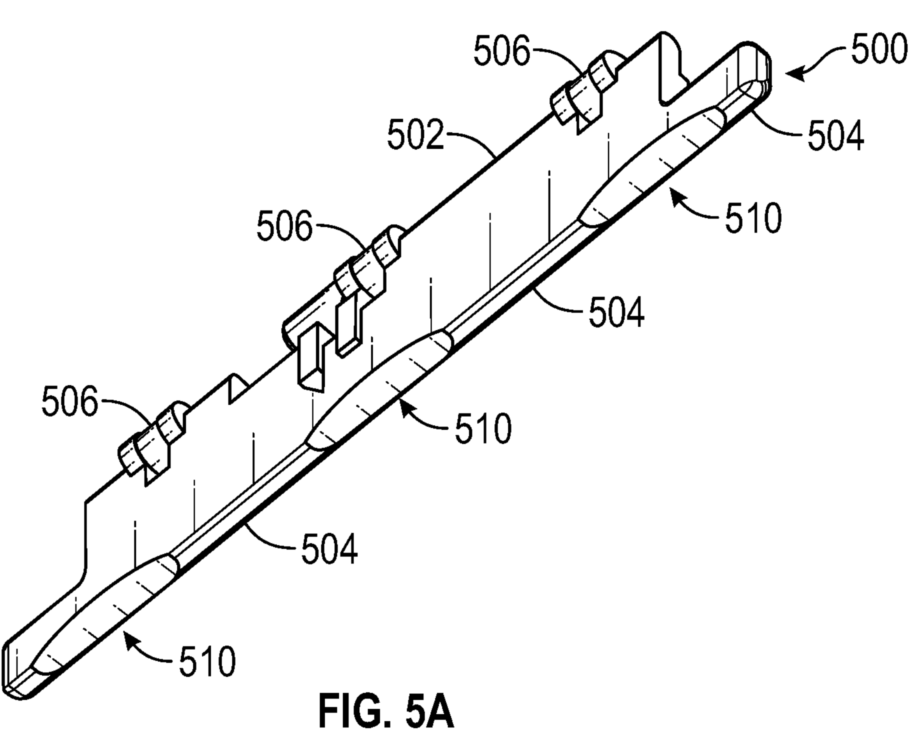
FIG. 5A is a perspective view of a retaining member.
Figure 5B:
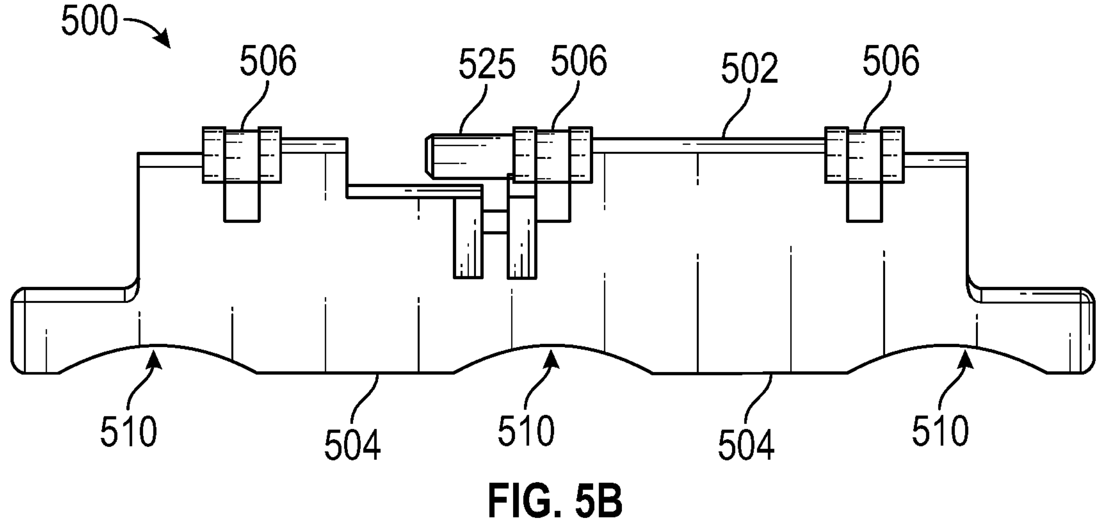
FIG. 5B is a front elevation view of the retaining member.

FIGS. 5A and 5B depict an example retaining member 500. Retaining member 500 is substantially planar and rectangular in this example and includes a top or first side 502 and bottom or second side 504 and is configured for attachment to corresponding attachment points 408 of the underside 406 of access cover 202 via fasteners 506 along the first side 502. The fasteners are configured for rotatable coupling to the attachment points 408 and the axis of rotation is transverse to the longitudinal axis of access cover 202, which permits the retaining member to move forward and backward relative to the longitudinal axis of the access cover 202, toward or away from the first and second ends 402, 404.

The second side 504 of retaining member 500 includes at least one profile 510 that includes a feature such as a cutout that accepts a portion of the outer profile of a household battery to be retained within cavity 302. In the depicted example the profile 510 is a semi-circular cutout corresponding or complementary to the outer circumference or profile of a AA household battery. In one example, the profile 510 is a barrier to prevent one or more batteries from moving towards the access cover. In another example, the profile is a resilient member that continually exerts a force on the battery such that the battery is pressed against bottom 602 of the battery compartment. In some examples, such as FIG. 9B, the bottom 602 may include one or more circumferential depressions corresponding to the outer circumference of one or more household batteries to allow the battery to seat in a more stationary position alone or in conjunction with the profile 510.

Figure 5C:
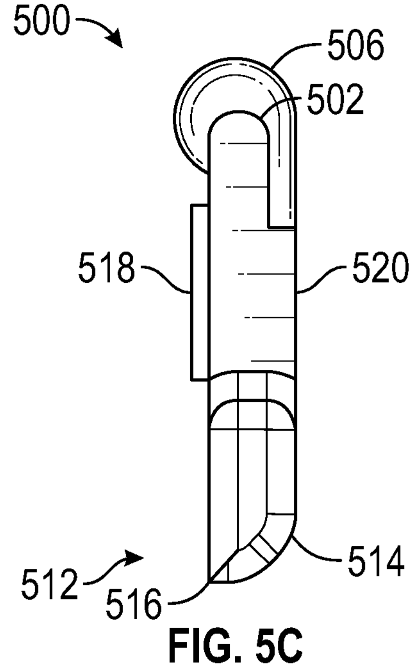
FIG. 5C is a side elevation view of the retaining member.

Referring to FIG. 5C, the second side includes an edge 512. Edge 512 may be flat or rounded or may include a tapered or angled portion 514 along a portion or the full width of the extending member. In one example tapered or angled portion 514 is angled from either the front side 518 or back side 520 of retainer member 500 forming a tip 516. As shown in FIG. 5C, the tip 516 is formed to the front side 518.

Figure 5D:
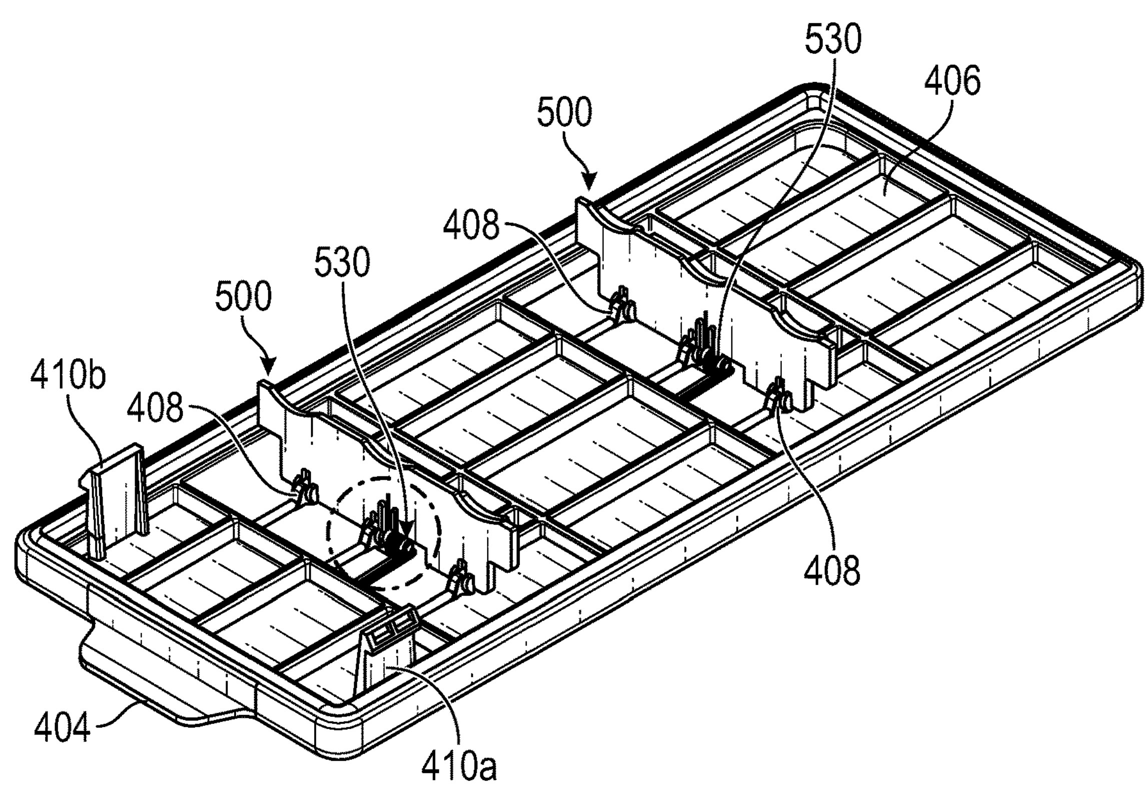
FIG. 5D is a bottom perspective view of the access cover showing the retaining members.
Figure 5E:
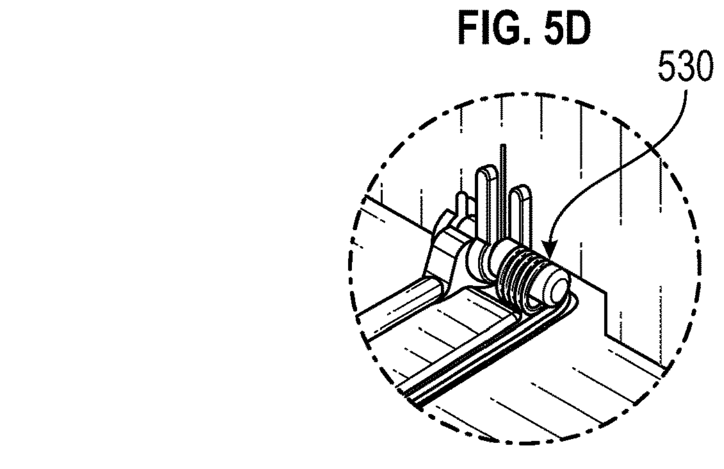
FIG. 5E is a detailed perspective view showing the biasing member of the retaining member according to an example.
Figure 5F:
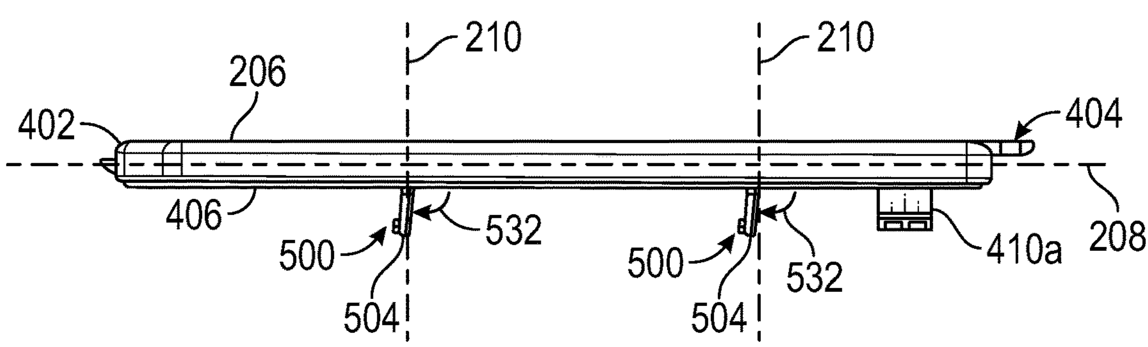
FIG. 5F is a side elevation view of the access cover showing the retaining members in a fully extended position.
Figure 5G:
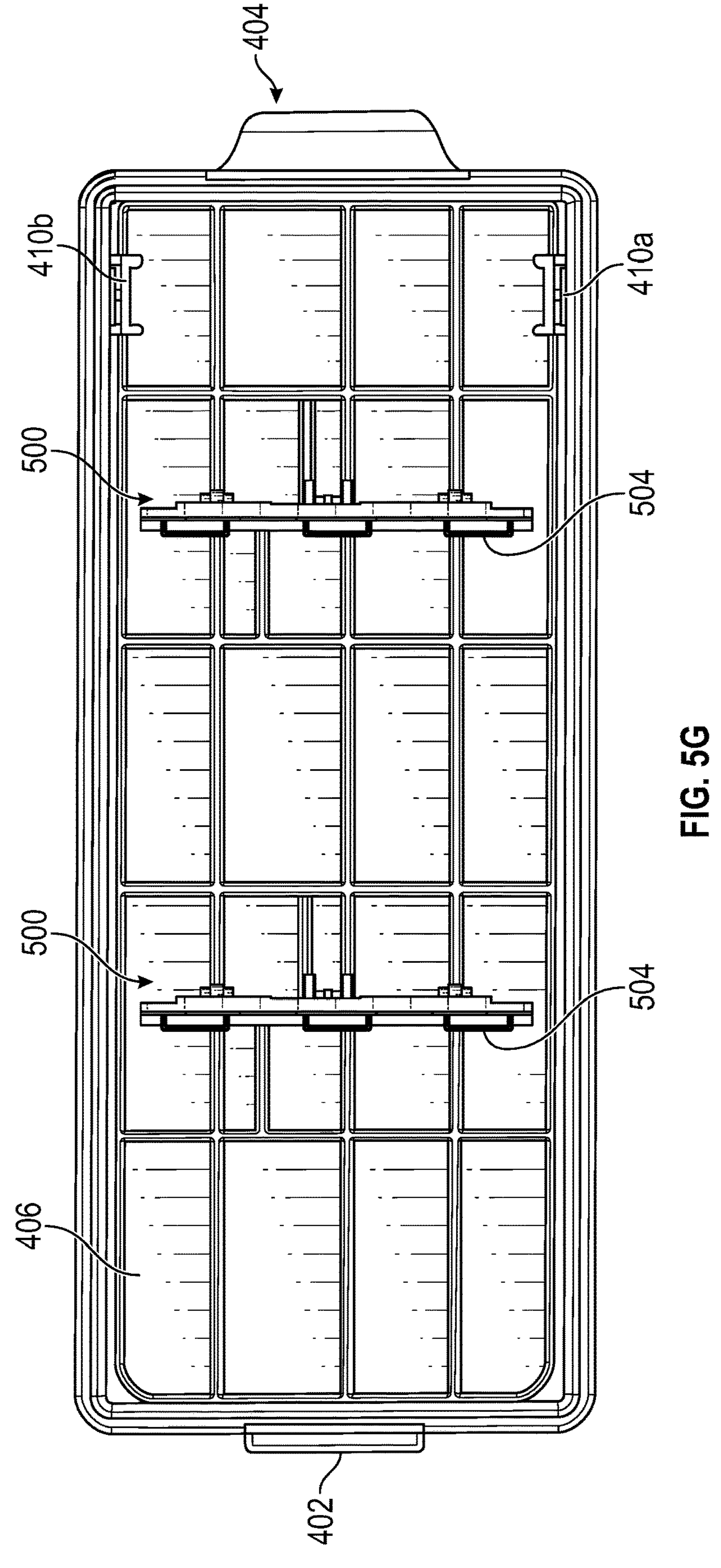
FIG. 5G is a bottom plan view of FIG. 5F.

FIGS. 5D and 5E depict biasing member 530. Biasing member 530 couples the retaining member 500 to the underside 406 of the access cover 202 and urges the retaining member to an extended position away from the underside 406 of the access cover. In one example the retaining member 500 is substantially planar and lies in a plane perpendicular to the surface of the underside 406 of the access cover 202 when extended. In one example the biasing member is a spring coiled around a shaft 525 received by an attachment point 408 and positioned parallel to and in some instances coextensive with side 502 of retaining member 500. One end of the coiled spring is attached to the retaining member 500 and the other end of the spring is attached to underside 406 of the access cover. In one example biasing member 530 urges the retaining member in a fully extended position. As shown in FIGS. 5F and 5G, in one aspect, in its fully extended position, the retaining member extends past a right angle such that the tapered portion 514 of the retaining member at least partially abuts a battery. If the battery starts to unseat it will press the retaining member harder against its stop. In some aspects, the retaining member extends at an angle (denoted 532) of between 92 and 100 degrees with respect to the surface of the underside 406 of the access cover or longitudinal axis 208. Vertical axis 210 which intersects longitudinal axis 208 at a right angle (90 degrees) is also shown for clarity.

Figure 6A:
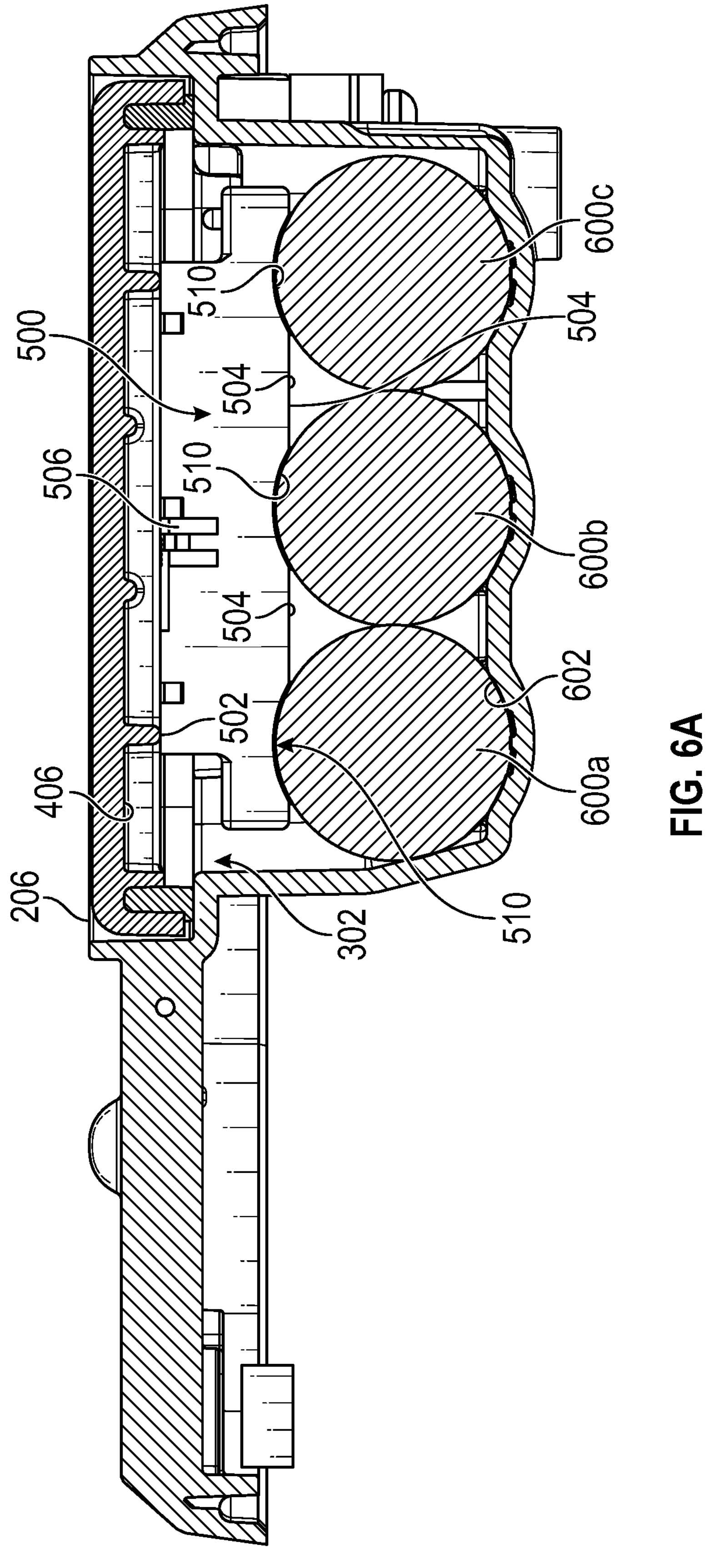
FIG. 6A is a cross-sectional at line A-A of FIG. 2 of a household battery configuration with household batteries installed.
Figure 6B:
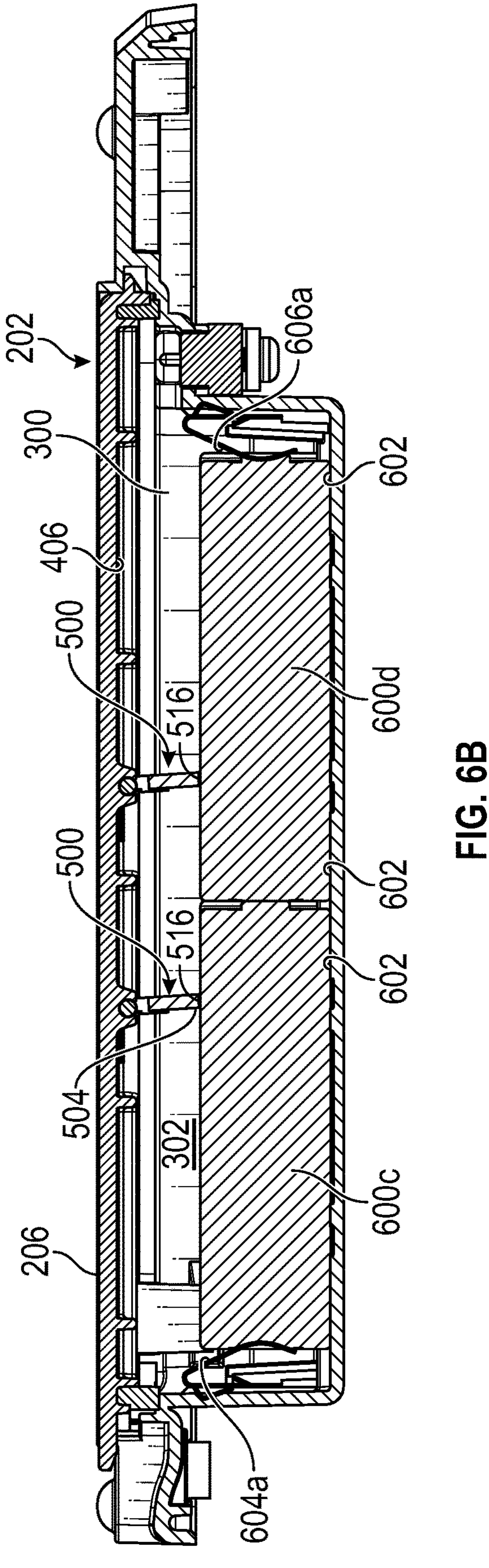
FIG. 6B is a lengthwise-section at line B-B of FIG. 2 of a household battery configuration with household batteries installed.

FIG. 6A is a cross-sectional view at line A-A of FIG. 2 that depicts a household battery configuration with household batteries 600*a*, 600*b*, 600*c* installed in the battery compartment 300. The access cover 202 is in a closed position and retaining member 500 is in an extended position to prevent the batteries from moving toward the access cover. FIG. 6B is a lengthwise-section at line B-B of FIG. 2 of the configuration shown in FIG. 6A and showing a second row of batteries and battery 600*d*.

The battery compartment 300 additionally includes electrical connectors for the household batteries. The electrical connectors include a first electrical connector and a second electrical connector 604*a,b* on one side of the cavity and a third electrical connector and a fourth electrical connector 606*a,b* on an opposite side of the cavity. The first and second electrical connectors and each include a conductive surface that is electrically coupled to electronics within the pump 100. The third and fourth electrical connectors and each include a conductive, leaf spring that is also electrically coupled to electronics within the pump 100. When household batteries are installed in the pump 100, the electrical connectors both provide electrical connection between the batteries and the electronics of the pump 100 and constrain movement of the batteries in the longitudinal direction. When a battery pack is installed, the electrical connectors constrain movement of the battery pack in the longitudinal direction, but do not provide an electrical connection between the battery pack and the electronics of the pump 100. Rather, the connector provides electrical connection between the battery pack and the electronics of the pump 100.

Figure 7A:
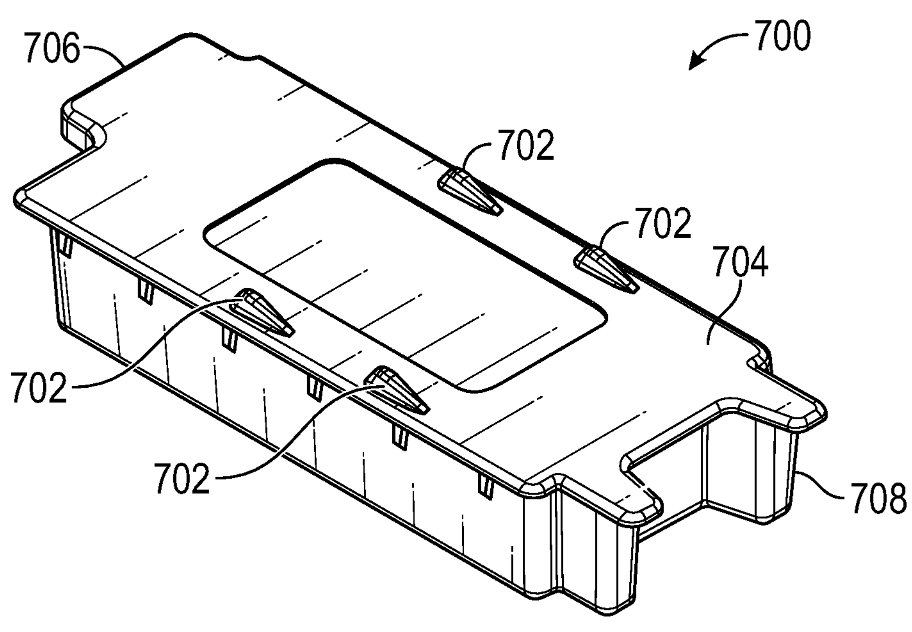
FIG. 7A is a top perspective view of the battery pack in an example configuration showing protrusions.
Figure 7B:
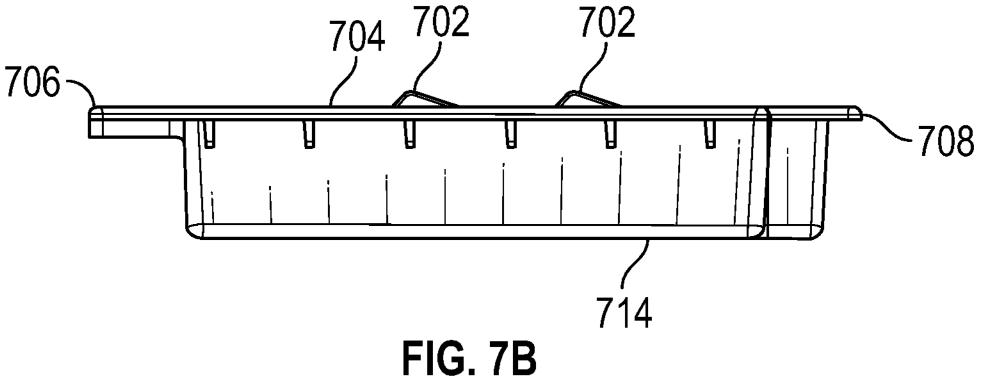
FIG. 7B is a side elevation view of the battery pack with the protrusions visible.

FIGS. 7A and 7B are top perspective and side views of battery pack 700 in an example configuration. Protrusions 702 are further depicted on the top surface 704 of the battery pack. At least one protrusion is configured to engage and displace at least one retaining member. The battery pack has a first end 706 that, when placed is in the compartment, corresponds to the first end of the battery compartment and a second end 708 that similarly corresponds to the second end of the battery compartment. The battery pack also has a bottom surface 714 that is substantially adjacent to and partially abuts the bottom of the battery compartment (see FIG. 9A). In one example one or more protrusions have an angled or sloping top surface 710 oriented such that it causes one or more retaining members second side to move in a direction opposite the force exerted by the biasing member as the access cover is rotated into a closed position. The second side of the retaining member may be secured in abutting engagement with at least one of the plurality of household batteries or the battery pack. The second end of the access cover may also be latched to the second end of the battery compartment. In another example the top surface of the protrusions includes an angled or sloping portion 710 and further a flat portion 712 that may abut the underside of the access cover when closed. In one example the angle of surface or portion 710 may be configured for mating engagement with edge tapered portion 514 of retaining member 500 as access cover 202 is closed.

Figure 8:
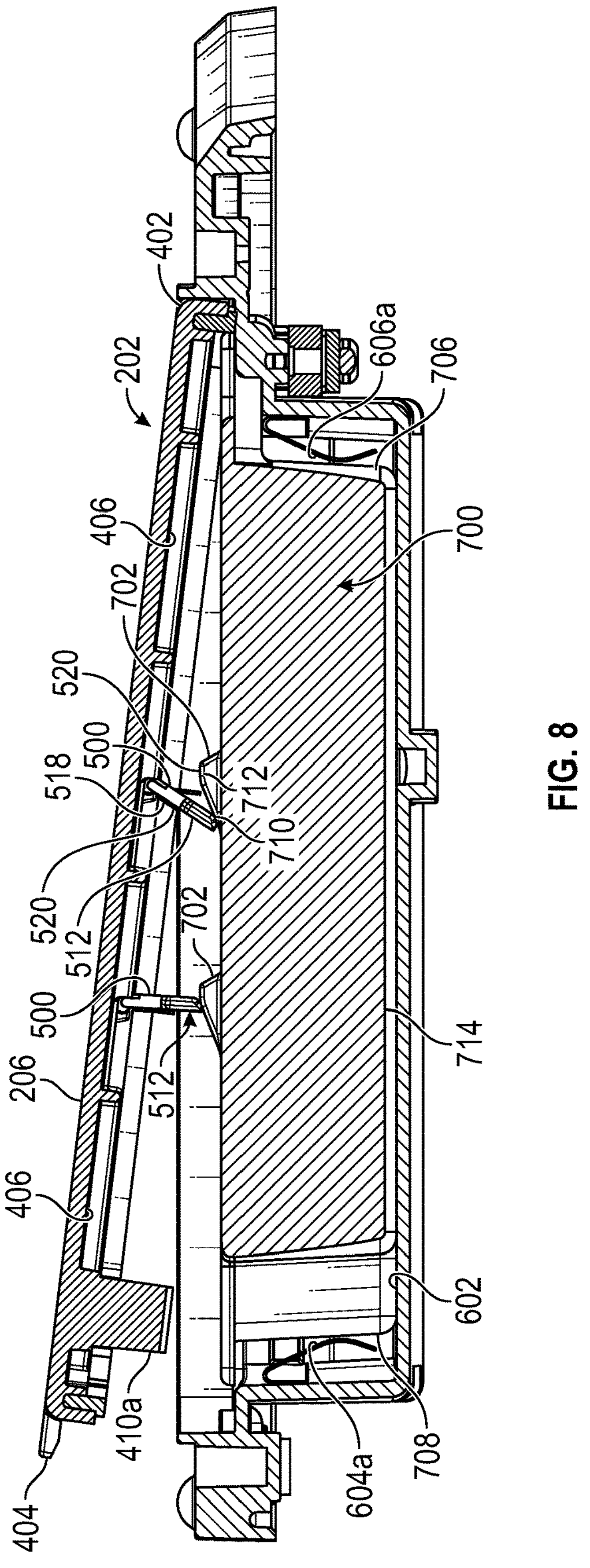
FIG. 8 is a longitudinal sectional at line B-B of FIG. 2 of the battery pack with the retainer protrusions visible.

FIG. 8 is a side sectional view of the battery pack with the protrusions visible with the access cover partially closed and retaining members engaging the protrusions. As the access cover is closed, it causes one or more retaining members to fold. In one example the extended retaining member strikes the surface of the protrusion at an obtuse angle, causing the retaining member to shunt out of the way so that the retaining member lies substantially parallel to the top surface 704 of the battery pack when the access cover is closed. The first side of the folded retaining member may rest on a protrusion when the access cover is closed.

Figure 9A:
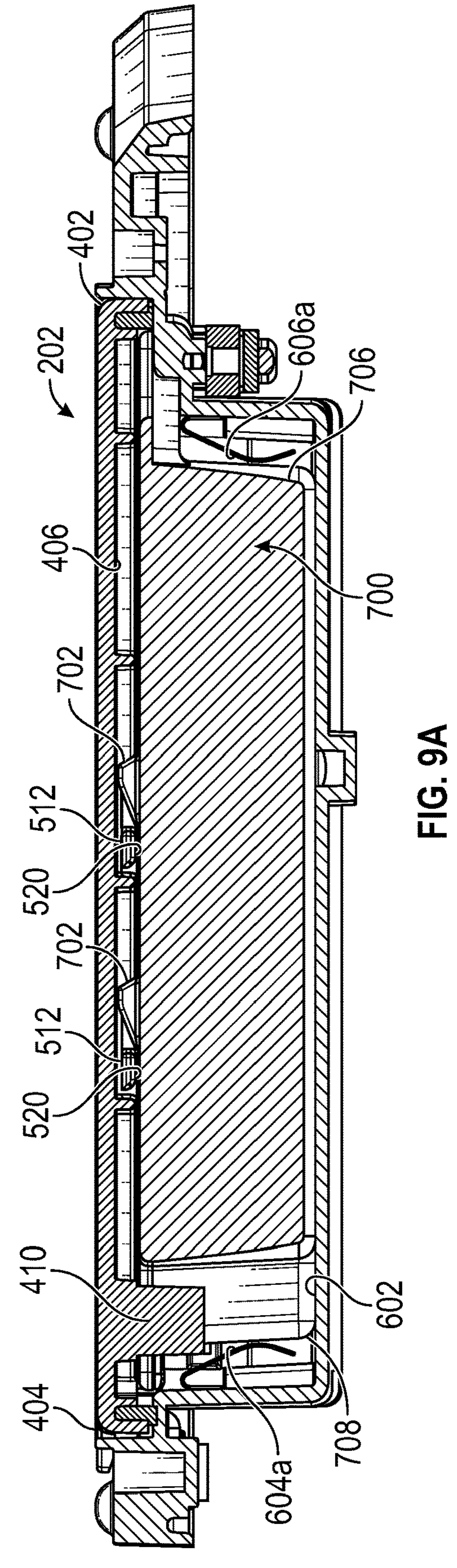
FIG. 9A is a longitudinal section at line B-B of FIG. 2 in a battery pack configuration with the battery pack installed.
Figure 9B:
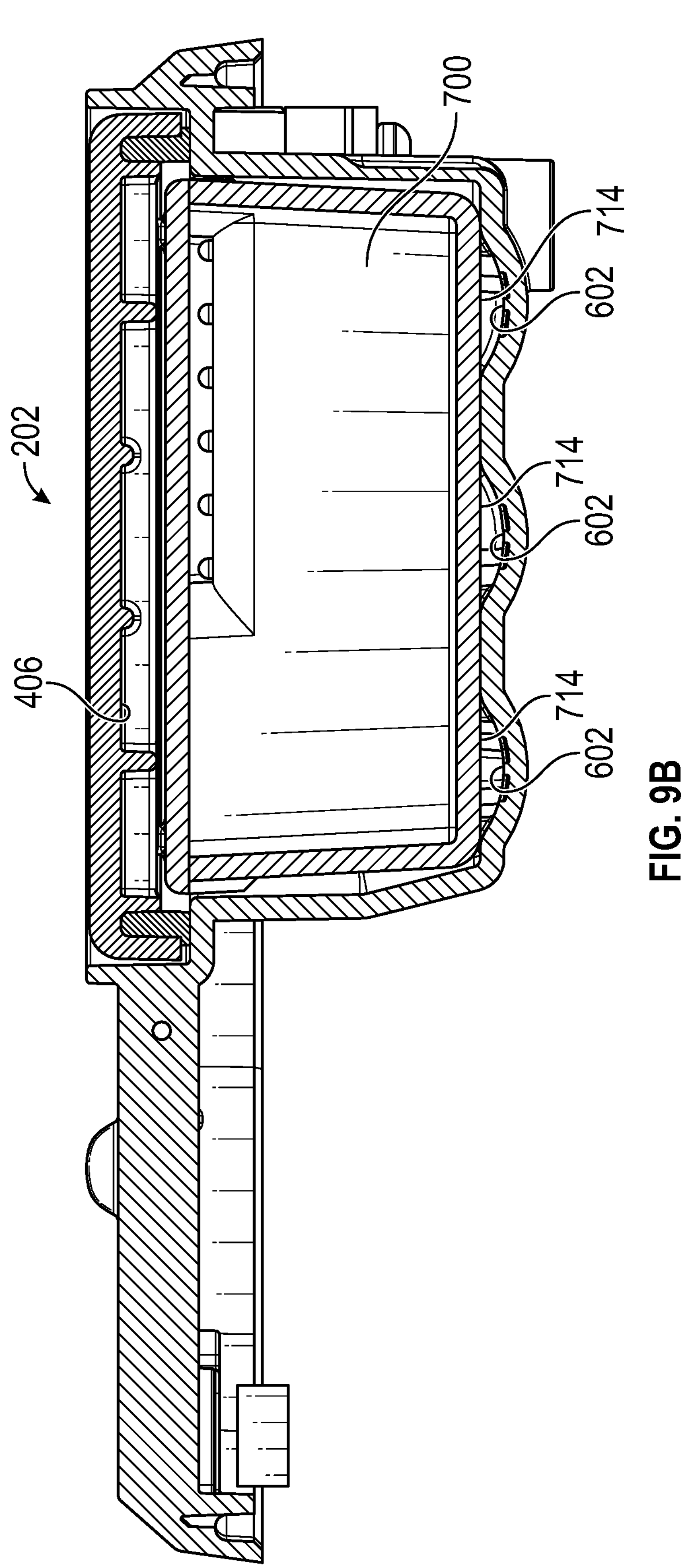
FIG. 9B is a cross-section at line A-A of FIG. 2 in a battery pack configuration with the battery pack installed.

FIG. 9A is a side sectional view at line B-B of FIG. 2 in a battery pack configuration with the battery pack 700 installed in battery compartment 300 with the access cover 202 closed. FIG. 9B is a cross-sectional view at line A-A of FIG. 2 in a battery pack configuration with the battery pack 700 installed in battery compartment 300 with the access cover 202 closed. In these views, the retaining members 500 are in their nonextended or folded position.

The terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as +10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. An ambulatory pump comprising:

a pump;

a controller coupled to the pump for controlling the pump to deliver fluid to a patient;

a battery compartment electrically coupled to the pump and the controller, the battery compartment defining a cavity for alternately receiving a battery pack and a plurality of household batteries, each of the plurality of batteries having a diameter and a substantially circumferential profile;

an access cover configured to engage the battery compartment and cover the cavity of the battery compartment when in a closed position, the access cover having an outer surface facing away from the battery compartment and an underside facing the cavity when the access cover is engaged with the battery compartment; and at least one substantially planar retaining member, the least one retaining member comprising a first side and a second side opposite the first side, wherein the first side is rotatably coupled to the underside of the access cover and the second side having has a profile configured to engage at least one of the plurality of household batteries when the access cover is engaged with the battery compartment in the closed position.

2. The ambulatory pump of claim 1, wherein the profile of the second side includes at least one semi-circular portion configured for abutting engagement of at least one battery of the plurality of household batteries.

3. The ambulatory pump of claim 2, wherein the retaining member holds the at least one battery in place within the cavity.

4. The ambulatory pump of claim 1 further comprising a biasing member, wherein the biasing member is configured for connection to the access cover and the at least one retaining member, the biasing member urging the second side to extend away from the access cover.

5. The ambulatory pump of claim 4, wherein each retaining member has a corresponding biasing member.

6. The ambulatory pump of claim 4, wherein the biasing member is a spring.

7. The ambulatory pump of claim 1, the at least one substantially planar retaining member comprising a plurality of retaining members, each retaining member corresponding to a position of at least one household battery within the cavity.

8. The ambulatory pump of claim 1, wherein the battery pack comprises a substantially flat top surface and a bottom surface, wherein the access cover in its closed position faces the top surface of the battery pack when positioned within the cavity.

9. The ambulatory pump of claim 8, the access cover further comprising a first end and a second end, and the battery compartment has corresponding first and second ends, wherein the access cover first end is configured for releasable rotatable coupling to the battery compartment first end and the access cover second end is configured for releasable coupling to the battery compartment second end.

10. The ambulatory pump of claim 9, wherein the access cover is moved from an open position to a closed position by coupling the access cover first end to the compartment first end and rotating the access cover second end toward the compartment second end.

11. The ambulatory pump of claim 10, the access cover further comprising a biasing member configured for connection to the at least one retaining member and bias of the second side to extend away from the access cover, wherein the top surface of the battery pack comprises at least one protrusion configured to displace at least one retaining member second side in a direction opposite a force exerted by the biasing member as the access cover is moved to the closed position.

12. The ambulatory pump of claim 11, wherein the protrusion has an angled surface that engages the at least one retaining member second side.

13. The ambulatory pump of claim 11, wherein the protrusion causes the retaining member to fold as the access cover is moved to the closed position.

14. The ambulatory pump of claim 13, wherein the at least one retaining member abuts the top surface of the battery pack.

15. A method comprising:

providing a battery compartment electrically coupled to a pump and a controller, wherein the controller is coupled to the pump for controlling the pump to deliver fluid to a patient, the battery compartment defining a cavity for alternately receiving a battery pack and a plurality of household batteries, each of the plurality of household batteries having a diameter and a substantially circumferential profile;

inserting at least one of the plurality of household batteries or the battery pack within the battery compartment;

releasably attaching a first end of an access cover to a first end of the battery compartment, the access cover configured to cover the battery compartment and having a second end and an underside, the underside facing the cavity when the access cover is in a closed position and including at least one retaining member, the at least one retaining member having a first side and a second side opposite the first side, wherein the first side is rotatably coupled to the underside of the access cover and the second side is configured to abut the plurality of household batteries or the battery pack in the closed position;

rotating the access cover to the closed position;

securing the second side of the retaining member in abutting engagement with the at least one of the plurality of household batteries or the battery pack; and latching the second end of the access cover, wherein the access cover second end corresponds to a second end of the battery compartment, to the battery compartment second end.

16. The method of claim 15, wherein the second side has a profile configured to engage at least one of the plurality of household batteries when the access cover is in the closed position.

17. The method of claim 15, the access cover further comprising a biasing member, wherein the biasing member is configured to bias the second side of the retainer away from the access cover.

18. The method of claim 15, the battery pack further comprising a top surface having at least one protrusion, wherein the step of rotating the access cover causes the at least one protrusion to displace the second side of the at least one retaining member.

19. The method of claim 18, wherein protrusion has a sloping top surface causing the displaced at least one retaining member to fold so that the retaining member lies substantially parallel to the top surface of the battery pack when the access cover is closed.

20. The method of claim 15, wherein the at least one retaining member has a substantially circumferential profile complementary to the at least one of the plurality of household batteries.

* * * * *